United States Patent
Menendez et al.

(10) Patent No.: US 9,597,094 B2
(45) Date of Patent: Mar. 21, 2017

(54) SURGICAL PROCESS FOR ANTERIOR HIP REPLACEMENT

(71) Applicant: Tedan Surgical Innovations, LLC., Sugar Land, TX (US)

(72) Inventors: Lawrence Richard Menendez, Manhattan Beach, CA (US); Daniel C. Allison, Studio City, CA (US); Daniel Bass, Half Moon Bay, CA (US); Bob Mastny, Palm Bay, CA (US); Terry Johnston, Redwood City, CA (US)

(73) Assignee: TEDAN SURGICAL INNOVATIONS, LLC., Sugar Land, TX (US)

( * ) Notice: Subject to any disclaimer, the term of this patent is extended or adjusted under 35 U.S.C. 154(b) by 213 days.

(21) Appl. No.: 14/461,809

(22) Filed: Aug. 18, 2014

(65) Prior Publication Data

US 2014/0358149 A1 Dec. 4, 2014

Related U.S. Application Data

(62) Division of application No. 13/364,497, filed on Feb. 2, 2012, now Pat. No. 8,808,176.

(51) Int. Cl.
*A61B 17/17* (2006.01)
*A61B 17/02* (2006.01)

(52) U.S. Cl.
CPC ............ *A61B 17/175* (2013.01); *A61B 17/02* (2013.01)

(58) Field of Classification Search
CPC ........ A61B 17/02–17/0206; A61B 2017/0275; A61B 17/175; A61B 17/1742
See application file for complete search history.

(56) References Cited

U.S. PATENT DOCUMENTS

| | | | |
|---|---|---|---|
| 3,810,462 A | 5/1974 | Szpur |
| 4,143,652 A | 3/1979 | Meier et al. |
| 4,617,916 A | 10/1986 | Levahn et al. |
| 4,813,401 A | 3/1989 | Grieshaber |
| 4,867,404 A | 9/1989 | Harrington et al. |
| 5,704,900 A | 1/1998 | Dobrovolny et al. |
| 6,511,423 B2 | 1/2003 | Farley |

(Continued)

OTHER PUBLICATIONS

Front Mount Nathanson StrongArm Liver Retraction System, Mediflex Surgical Products, http://www.mediflex.com/app/pc/configurePrd.asp?IDProduct=3888&idCategory=61.

*Primary Examiner* — David Bates
*Assistant Examiner* — Olivia C Chang
(74) *Attorney, Agent, or Firm* — Kramer Amado P.C.

(57) ABSTRACT

Various exemplary embodiments relate to a method of performing an anterior approach hip replacement. The method may include: exposing a surgical site including the femoral neck and acetabulum using a plurality of retractors secured to the plurality of accessory arms; cutting the femoral neck to remove the femoral head; preparing the acetabulum for insertion of an acetabular cup; preparing the femur for insertion of a femoral implant by lifting the femur using a femur hook and the femur distractor; and closing the surgical site. In various alternative embodiments, the method may include using a lesser trochanteric retractor coming from a direct medial approach and a greater trochanteric retractor coming from a lateral, posterior, proximal approach.

13 Claims, 4 Drawing Sheets

(56) References Cited

U.S. PATENT DOCUMENTS

| | | | |
|---|---|---|---|
| 6,626,830 B1 | 9/2003 | Califlore et al. | |
| 6,860,877 B1 | 3/2005 | Sanchez et al. | |
| 7,338,442 B2 | 3/2008 | Mulac et al. | |
| 7,458,933 B2 | 12/2008 | Levahn et al. | |
| 7,753,844 B2 | 7/2010 | Sharratt et al. | |
| 2005/0119697 A1 | 6/2005 | Sharratt | |
| 2005/0171548 A1* | 8/2005 | Kelman | A61B 17/1604 606/79 |
| 2006/0030947 A1* | 2/2006 | Mears | A61B 17/00234 623/22.11 |
| 2007/0093696 A1 | 4/2007 | Sharratt | |
| 2012/0226361 A1* | 9/2012 | Podolsky | A61B 17/164 623/22.15 |

\* cited by examiner

SURGICAL PROCESS FOR ANTERIOR HIP REPLACEMENT

This application is a divisional of U.S. Ser. No. 13/364,497 filed on Feb. 2, 2012, the entire disclosure of which is hereby incorporated herein for all purposes.

FIELD OF THE INVENTION

Some embodiments of the invention relate to the field of orthopedic surgery. Further, to the method of anterior hip replacement surgery.

BACKGROUND OF THE INVENTION

Hip replacement surgery may be necessary for a patient suffering from various conditions. Prosthetic implants may be used to replace a defective hip joint. A hip replacement surgery may involve removing a portion of the femur and/or acetabulum and inserting a prosthetic implant. During such procedures, it is known to use retractors in order to hold soft tissue in a position that permits the position to access the surgical site. In one common practice, a single retractor, or a number of retractors, will each be manually supported by an assistant. In these systems, the assistant will hold the retractor in position, and may apply a force against the soft tissue at the same time. In the case of relatively complex procedures such as hip replacement surgery, it may be necessary to use two or even a larger number of separate retractors, which may necessitate two or more assistants to manually operate the retractors. This may at some times be somewhat cumbersome.

SUMMARY OF THE INVENTION

In light of the present need for a surgical process for anterior hip replacement, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various exemplary embodiments relate to a method of performing an anterior approach hip replacement using a retractor assembly. The method may include: providing a retractor assembly including a first vertical post, a plurality of accessory arms mounted to the first vertical post, a second vertical post, and a femur distractor mounted to the second vertical post; exposing a surgical site including the femoral neck and acetabulum using a plurality of retractors secured to the plurality of accessory arms; cutting the femoral neck to remove the femoral head; preparing the acetabulum for insertion of an acetabular cup; preparing the femur for insertion of a femoral implant by lifting the femur using a femur hook and the femur distractor; and closing the surgical site.

In various alternative embodiments, the step of providing a retractor assembly may include: mounting the first vertical post to a rail on the non-operative side of the table; mounting a t-bar to the first vertical post; mounting a proximal accessory arm to the t-bar; mounting a middle accessory arm to the t-bar; and mounting a distal accessory arm to the t-bar. The step of providing a retractor assembly may also include: mounting the second vertical post to the operative side of the table approximately 10 inches distal to the hip joint; mounting an angled arm to the second vertical post; and mounting a ratchet femur distractor to the arm.

In various alternative embodiments, the step of exposing a surgical site comprises: making an incision from a spot approximately one fingerbreadth distal and lateral to the anterior superior iliac spine directed toward the lateral thigh, approximately 8-12 cm in length; placing a first hohmann retractor underneath the rectus femoris muscle; retracting the sartoris and rectus femoris muscles medially; securing the first hohmann retractor in place by attaching the first hohmann retractor to a first accessory arm; placing a second hohmann retractor around the medial femoral neck; securing the second hohmann retractor to a second accessory arm; placing a third right-angled hohmann retractor laterally around the lateral femoral neck; and securing the third right-angled hohmann retractor to a third accessory arm. The step of exposing the surgical site may also include: making an L-shaped capsulotomy in the hip capsule forming a capsular flap; tagging the capsular flap with two sutures; and securing each of the two sutures to the retractor assembly.

In various alternative embodiments, the step of cutting the femoral neck may include: placing the second hohmann retractor directly on the bone around the medial femoral neck; securing the second hohmann retractor using the second accessory arm; placing the third hohmann retractor directly on the bone around the lateral femoral neck; securing the third hohmann retractor using the third accessory arm; and cutting the femoral neck with an oscillating saw.

In various alternative embodiments, the step of preparing the acetabulum comprises: placing a first hohmann retractor at the center of the posterior wall; levering the femur posteriorly using the first hohmann retractor; securing the first hohmann retractor to a first accessory arm; placing a second hohmann retractor at the superior anterior wall; securing the second hohmann retractor to a second accessory arm; placing a third hohmann retractor at the inferior anterior wall; securing the third hohmann retractor to a third accessory arm; and reaming the acetabulum.

In various alternative embodiments, the step of preparing the femur may include: placing a J-hook around the proximal femur at a point distal to the lesser trochanter; securing the J-hook to the femur distractor; and elevating the femur using the femur distractor. The step of preparing the femur may also include: mounting a horizontal side bar to the second vertical side post such that the horizontal side bar is directed proximally; mounting an accessory arm to the horizontal side bar; placing a trochanteric retractor behind the greater trochanter; and securing the trochanteric retractor to the accessory arm. The step of preparing the femur may also include dropping the distal end of the table such that the hip joint is extended approximately 30-60 degrees; placing a two-pronged stout retractor medially over the lesser trochanter; and securing the two-pronged stout retractor to the first accessory arm. The step of preparing the femur may also include: placing a femoral clamp directly on the proximal femoral shaft; rotating the femur using the femoral clamp; and securing the femoral clamp to the first vertical post. The step of preparing the femur may also include placing a loop around the thigh; adducting the hip using the loop; and securing the loop to the first vertical post.

Various exemplary embodiments relate to a method of preparing the femur for an anterior approach hip replacement using a retractor assembly. The method may include: providing a retractor assembly including a first vertical post, a plurality of accessory arms mounted to the first vertical post, a second vertical post, and a femur distractor mounted to the second vertical post; exposing a surgical site including the femoral neck using a plurality of retractors secured to the plurality of accessory arms; cutting the femoral neck to remove the femoral head; placing a J-hook around the proximal femur at a point distal to the lesser trochanter; securing the J-hook to the femur distractor; and elevating the femur using the femur distractor.

In various alternative embodiments, the method of preparing the femur may also include: mounting a horizontal side bar to the second vertical post such that the horizontal side bar is directed proximally; mounting an accessory arm to the horizontal side bar; placing a trochanteric retractor behind the greater trochanter; and securing the trochanteric retractor to the accessory arm.

In various alternative embodiments, the method of preparing the femur may also include: dropping the distal end of the table such that the hip joint is extended approximately 30-60 degrees; placing a two-pronged stout retractor medially over the lesser trochanter; and securing the two-pronged stout retractor to the first accessory arm.

In various alternative embodiments, the method of preparing the femur may also include: placing a femoral clamp directly on the proximal femoral shaft; rotating the femur using the femoral clamp; and securing the femoral clamp to the first vertical post.

In various alternative embodiments, the method of preparing the femur may also include: placing a loop around the thigh; adducting the hip using the loop; and securing the loop to the first vertical post.

Various exemplary embodiments relate to a method of preparing the acetabulum for an anterior approach hip replacement using a retractor assembly, the method comprising: providing a retractor assembly including a first vertical post, a plurality of accessory arms mounted to the first vertical post, a second vertical post, and a femur distractor mounted to the second vertical post; placing a first hohmann retractor at the center of the posterior wall; levering the femur posteriorly using the first hohmann retractor; securing the first hohmann retractor to a first accessory arm; placing a second hohmann retractor at the superior anterior wall; securing the second hohmann retractor to a second accessory arm; placing a third hohmann retractor at the inferior anterior wall; securing the third hohmann retractor to a third accessory arm; and reaming the acetabulum.

In various alternative embodiments, the method of preparing the acetabulum may also include placing an acetabular cup in the reamed acetabulum using fluoroscopic guidance.

The foregoing objects and advantages of the invention are illustrative of those that can be achieved by the various exemplary embodiments and are not intended to be exhaustive or limiting of the possible advantages that can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

BRIEF DESCRIPTION OF THE DRAWINGS

In order to better understand various exemplary embodiments, reference is made to the accompanying drawings, wherein.

DETAILED DESCRIPTION OF THE PREFERRED EMBODIMENTS OF THE INVENTION

Figure 1:
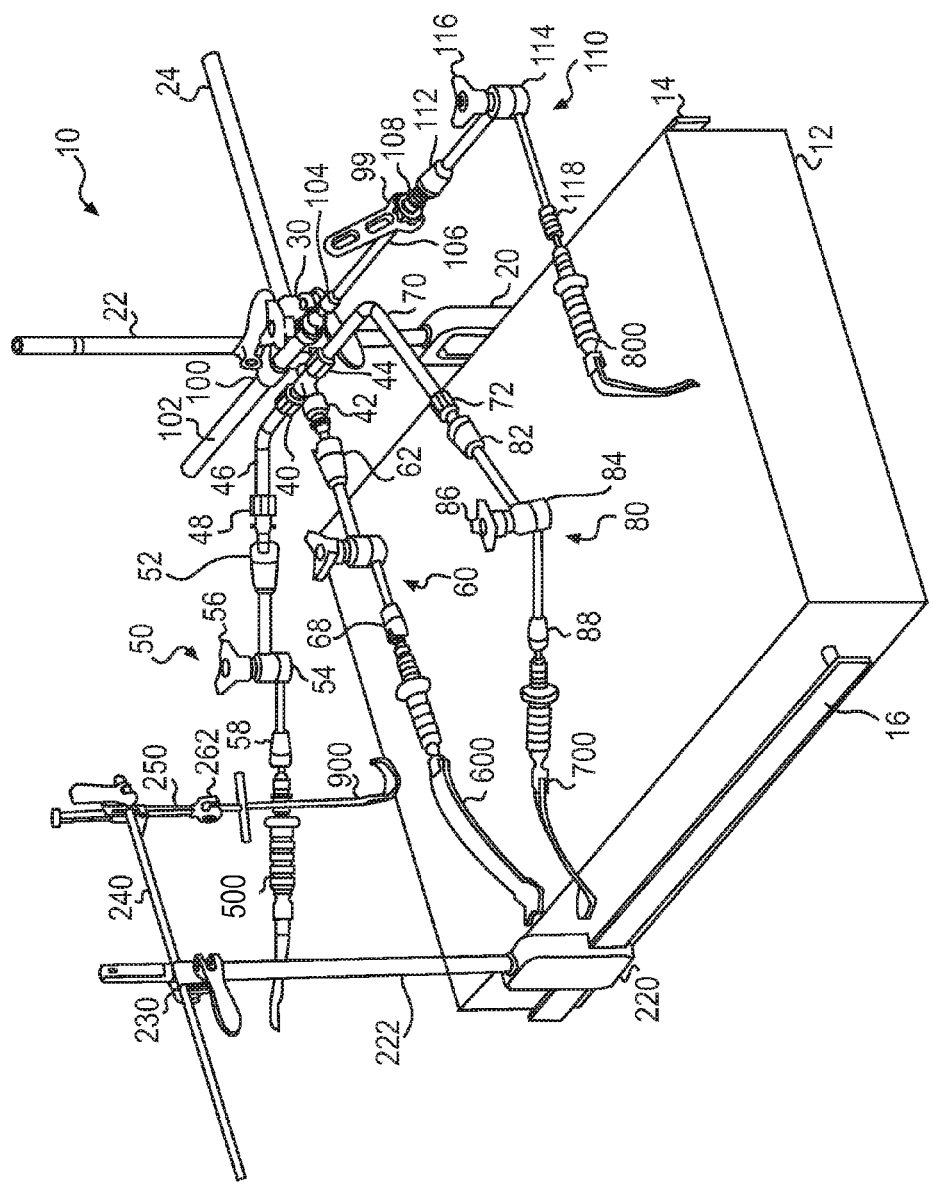
FIG. 1 illustrates an exemplary retractor assembly for performing an anterior approach hip replacement.

A hip replacement may be performed from various approaches: posterior, lateral, or anterior. The posterior approach is used by most surgeons. The anterior approach offers the benefit of being a muscle sparing approach. Fewer muscles may be cut, leading to faster recovery times and minimizing the chances of post-operative dislocation. The anterior approach, however, may be more difficult in terms of exposure.

A retractor assembly for anterior approach hip replacement may improve exposure of the surgical site. Use of a retractor assembly may also reduce the required number of assistants for a hip replacement surgery. Without a retractor assembly, multiple assistants may be required to hold retractors during the surgical procedure. Assistants may crowd the operating area and reduce the surgeon's mobility and ability to use fluoroscopy. Assistants may also suffer from fatigue while holding a retractor, reducing exposure for the surgeon. Use of a retractor assembly may allow a surgeon to perform a hip replacement alone or with one assistant.

Use of a retractor assembly may increase exposure of the surgical site, making the anterior approach easier. A retractor assembly may help overcome difficulties of delivering the femur from the anterior approach. The greater exposure achieved from using a retractor assembly may allow standard implant systems to be used without modification.

Referring now to the drawings, in which like numerals refer to like components or steps, there are disclosed broad aspects of various exemplary embodiments.

FIG. 1 illustrates an exemplary retractor assembly 10 for performing an anterior approach hip replacement. A retractor assembly 10 is shown for use with an operating table 12. The operating table 12 is any suitable table such as, for example, an orthopedic table which has a hinged portion to help position the patient. The patient is not illustrated, but can recline, for example, in a supine position on the orthopedic table during surgery. The table 12 has longitudinal rails 14 and 16 as shown. These rails 14 and 16 provide a support for the retractor assembly 10.

A table clamp 20 is slidably mounted along the rail 14. The table clamp 20 supports a vertical side post 22. A T-post 24 is mounted to the post 22 on a clamp block 30.

A T-post 24 is supported by the clamp block 30 and can be moved longitudinally within the clamp block 30. The T-post 24 terminates in three quick connect ends 40, 42 and 44 respectively.

Mounted to the quick connect 40 is a small fixed angle arm 46. The small fixed angle arm 46 terminates on its own quick connect 48. Attached to the quick connect 48 is an accessory arm 50. The accessory arm 50 includes a connector 52, which connects to the quick connect 48, and which also has a ball and socket joint permitting a range of two-dimensional pivotal motion around the ball. The connector 52 may also include a ball and socket connection.

Each ball and socket connection includes a tightening lockdown feature to fix it at a desired angle. The accessory arm 50 also has a pivot 54 which can be locked in position by a handle 56. The accessory arm 50 terminates in a connector 58 which also has a ball turn fitting. This connector 58 is adapted to receive a retractor, such as the illustrated straight hohmann retractor 500.

Returning to the T-post 24, an accessory arm 60 is connected to the quick connect 42. This accessory arm 60 includes components 62, 64, 66 and 68 which correspond to items 52, 54, 56 and 58 described above. The accessory arm 64 thus supports a retractor, such as the illustrated femur retractor 600.

Returning to the T-post 24, connected to the quick connect 44 is a large fixed angle arm 70 that has at one end in its own quick connect 72, to which is connected another accessory arm 80. This accessory arm 80 includes components 82, 84, 86 and 88 which correspond to items 52, 54, 56 and 58 described above. The accessory arm 80 thus supports a retractor, such as the illustrated femur retractor 700.

Also supported on the post 22 by a clamp block 100 is an arm 102. In various alternative embodiments, arm 102 may be supported on post 222 as discussed in further detail below. The clamp block 100 is substantially similar in configuration to the clamp block 30. The arm 102 terminates at the ball joint 104 that supports an arm 106. A quick connect 108 leads to an accessory arm 110. The accessory arm 110 includes components 112, 114, 116 and 118 which correspond to components 52, 54, 56 and 58 as described above. The accessory arm 110 supports an angled hohmann retractor 800 as shown.

From the above, it will be appreciated that the above-described componentry provides for convenient positioning and locking of up to four retractors, 500, 600, 700 and 800. The wide range of degrees of freedom of are presented so that the retractors can be provisioned with a wide range of locations on the table at varying heights, and at varying spatial angles. Retractors are interchangeable and may be removed from an accessory arm and replaced with a different retractor. Also the arm 102 may be attached to post 222 instead of post 22.

Mounted to the rail 16 is a table clamp 220 which supports a vertical side post 222. A clamp block 230, similar to the clamp block 30, supports an arm 240. The arm 240 supports a ratcheting or rack and pinion femur distractor assembly 250. The hook connection 262 is adapted to support in a swinging fashion a J-hook 900. The J-hook 900 is adapted to support the weight of a femur. The J-hook 900 may be adapted with a pointed end to pierce the soft tissue surrounding the femur.

FIG. 1 also depicts a wrench 99 which is a movable tool that can be used to secure or release the quick connects.

Figure 2:
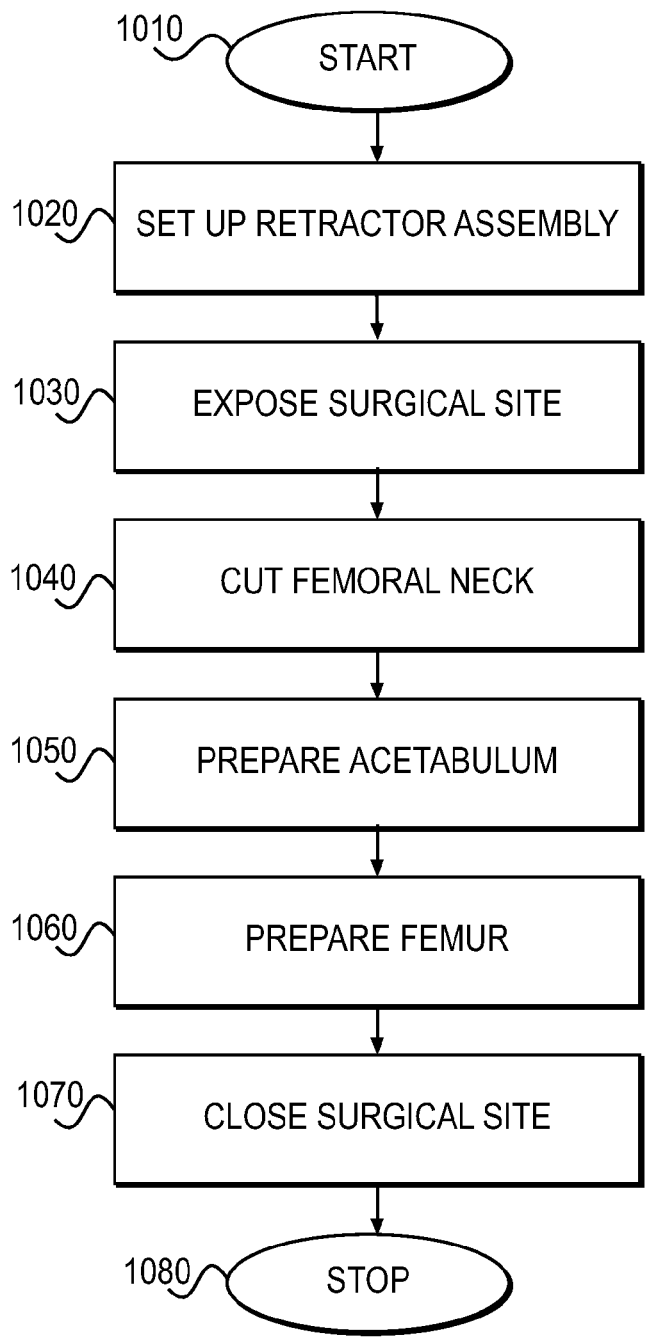
FIG. 2 illustrates a flow chart showing an exemplary method of performing an anterior approach hip replacement.

FIG. 2 illustrates a flow chart showing a method 1000 of performing an anterior approach hip replacement using a retractor assembly 10. Method 1000 may be performed by a surgeon alone or with one or more assistants. It should be understood that a step performed by the surgeon may be performed by one or more assistants acting under the direction of the surgeon. The surgeon may use retractor assembly 10 to perform method 1000 on a patient. The method 1000 may begin at step 1000 and proceed to step 1010.

In step 1010, the surgeon and/or assistants may set up the retractor assembly 10. The patient may be placed in a supine position on table 12. The patient's hips may be placed at the level of the bending joint of table 12. Both of the patient's lower extremities may be prepped and draped.

Post 22 may be secured to side rail 14 on the non-operative side of table 12 using table clamp 20. Post 22 may be located approximately 6 inches distal to the level of the patient's hip joint. T-post 24 may be mounted on post 20 using clamp block 30. The T-post 24 may be mounted approximately 10 inches above the level of the patient's skin. T-post 24 may extend toward the operative side of table 12. T-post 24 may be adjusted within clamp block 30 to extend the correct distance toward the operative side.

Small fixed angle arm 46 may be attached to T-post 24 at quick connect 40. Large fixed angle arm 70 may be attached to T-post 24 at quick connect 44. Accessory arm 50 may be attached to small fixed angle arm 46 at quick connect 48. Accessory arm 50 may be ready to receive a retractor 500 at connector 58. Accessory arm 60 may be attached to T-post 24 at quick connect 42. Accessory arm 60 may be ready to receive a retractor 60 at connector 68. Accessory arm 80 may be attached to large fixed angle arm 70 at quick connect 72. Accessory arm 80 may be ready to receive a retractor 700 at connector 78. When assembled, small fixed angle arm 46, large fixed angle arm 70, and accessory arms 50, 60, 80 may form a hemi-ring construct above the patient.

Vertical side post 222 may be secured to side rail 16 on the operative side of table 12 using table clamp 220. Vertical side post 222 may be located approximately 10 inches distal to the patient's hip joint. In various exemplary embodiments, arm 102 may be attached to vertical side post 222 using clamp block 100. In various alternative embodiments, arm 102 may be attached to post 22 using clamp block 100. In either case, arm 102 may be directed proximally. Accessory arm 110 may be attached to arm 102 at connector 108. Accessory arm 110 may be ready to receive a retractor 800.

Arm 240 may be mounted on vertical side post 222 using clamp block 230. Arm 240 may extend toward the non-operative side of table 12 and be placed at an upward sloping angle. Ratchet femur retractor 250 may be mounted on arm 240. Hook connection 262 may extend downward and be ready to receive J-hook 900. In various exemplary embodiments, vertical side post 222 may be mounted to table 12 after step 1050. The method 1010 may then proceed to step 1030.

In step 1030, the surgeon may expose the surgical site. The surgeon may make an incision from a spot approximately one fingerbreadth distal and lateral to the anterior superior iliac spine. The incision may extend toward the lateral thigh, approximately 8-12 cm in length. The surgeon may then bluntly develop the interval between the tensor fascia lata and sartorius muscles.

Next, the surgeon may place retractor 600 underneath the rectus femoris muscle on the medial side of the femoral neck. Retractor 600 may be a hohmann retractor. The surgeon may secure the hohmann retractor 600 to accessory arm 60. Accessory arm 60 may be moved to retract the sartorius and rectus femoris muscles medially. Accessory arm 60 may be locked in position by tightening handle 66. The surgeon may identify and ligate the lateral femoral circumflex artery and vein. Then the surgeon may elevate the indirect head of the rectus femoris muscle, revealing the underlying hip capsule.

The surgeon may then place retractor 600 medially around the medial femoral neck. Retractor 600 may be a straight hohmann retractor. The surgeon may secure the straight hohmann retractor 600 to accessory arm 60 and lock it in position. The surgeon may also place retractor 500 laterally around the lateral femoral neck. Retractor 500 may be a right-angled hohmann retractor. The surgeon may secure the right-angled hohmann retractor 500 to accessory arm 50 and lock it in position. The surgeon may then make an L-shaped capsulotomy in the hip capsule creating a capsular flap. The surgeon may tag the capsular flap with two sutures. Each suture may be secured to an appropriate hook on the hemi-ring construct to hold the capsular flap out of the way. Once the capsular flap is secured, the method 1000 may proceed to step 1040.

In step 1040, the surgeon may remove the femoral head by cutting the femoral neck. The surgeon may move lateral retractor 500 and medial retractor 600 so that they are placed directly on the bone of the femoral neck rather than the hip capsule. The surgeon may use fluoroscopy to determine the level of the femoral neck cut based on preoperative templating. The surgeon may use an oscillating saw to cut through the femoral neck. The surgeon may place a corkscrew drill into the femoral head. Using the corkscrew drill and a free retractor, the surgeon may remove the femoral head. In various alternative embodiments, the surgeon may make a parallel second cut in the femoral neck using the oscillating saw. The surgeon may remove the resulting "napkin ring" to provide extra room for removal of the femoral head. Once the femoral head is removed, the surgeon may remove lateral retractor 500 and medial retractor 600. The method may then proceed to step 1050.

In step 1050, the surgeon may prepare the acetabulum for the acetabular implant. The surgeon may expose the acetabulum using three retractors. The surgeon may place the first retractor 500 at the center of the posterior wall. In this step, retractor 500 may be a straight hohmann retractor or a curved hohmann retractor. The first retractor 500 may be secured to accessory arm 50. The surgeon may place the second retractor 600 at the superior anterior wall. In this step, retractor 600 may be a straight hohmann retractor, or curved hohmann retractor. The second retractor 600 may be secured to accessory arm 60. The surgeon may place the third retractor 700 at the inferior anterior wall. In this step, retractor 700 may be straight hohmann retractor, or curved hohmann retractor. The third retractor 700 may be secured to accessory arm 70. The surgeon may use the first retractor 500 to lever the femur posteriorly out of the way. The three retractors 500, 600, and 700 may be locked in place to provide optimal consistent exposure of the acetabulum.

The surgeon may clear the acetabulum of all pulvinar, labrum and debris. The surgeon may use fluoroscopy and one or more acetabular reamers to prepare the acetabulum. The surgeon may then place an acetabular cup or shell implant using fluoroscopy for guidance. Trial acetabular cups may be used. A liner may be placed inside the acetabular cup. Once the acetabular cup implant is placed, the three retractors 500, 600, and 700 may be removed. The method 1000 may then proceed to step 1060.

In step 1060, the surgeon may prepare the femur for the femoral implant. A brief summary of preparing the femur will be provided here. A method 2000 of preparing the femur will be described in greater detail below. The surgeon may set up vertical side post 222 before step 1060 as described above with regard to step 1010. Delaying the set up of vertical side post 222 until immediately before step 1060 may provide the surgeon with greater mobility during steps 1030, 1040, and 1050.

The surgeon may prepare the femur for insertion of a femoral implant including a neck piece and a head piece. The surgeon may first position the femur such that the femoral canal is exposed. The surgeon may position the femur using retractors 800 and 600, J-hook 900, a femoral clamp, and a lasso. Retractor assembly 10 may hold each device in position while the femur is exposed. The surgeon may then prepare the femoral canal using a box osteotome, canal finder, and increasing sized broaches. The surgeon may then insert the femoral implant. The surgeon may trial one or more implants to ensure proper placement. Once the implant is in place, the surgeon may reduce the hip.

In step 1070, the surgeon may close the surgical site. The surgeon may copiously irrigate the wound. The surgeon may expose the hip capsule using deep retractors such as Hibbs retractors. The deep retractors may be secured to accessory arms 50, 60, and/or 80. The surgeon may then close the capsulotomy in the hip capsule with large bore non-absorbable sutures. The surgeon may close the fascia with medium bore absorbable sutures. The surgeon may take care not to entrap the lateral femoral cutaneous nerve when closing the fascia. The surgeon may then close the skin using known methods. Once the incision has been closed, the method 1000 may proceed to step 1080, where the method ends.

Figure 3:
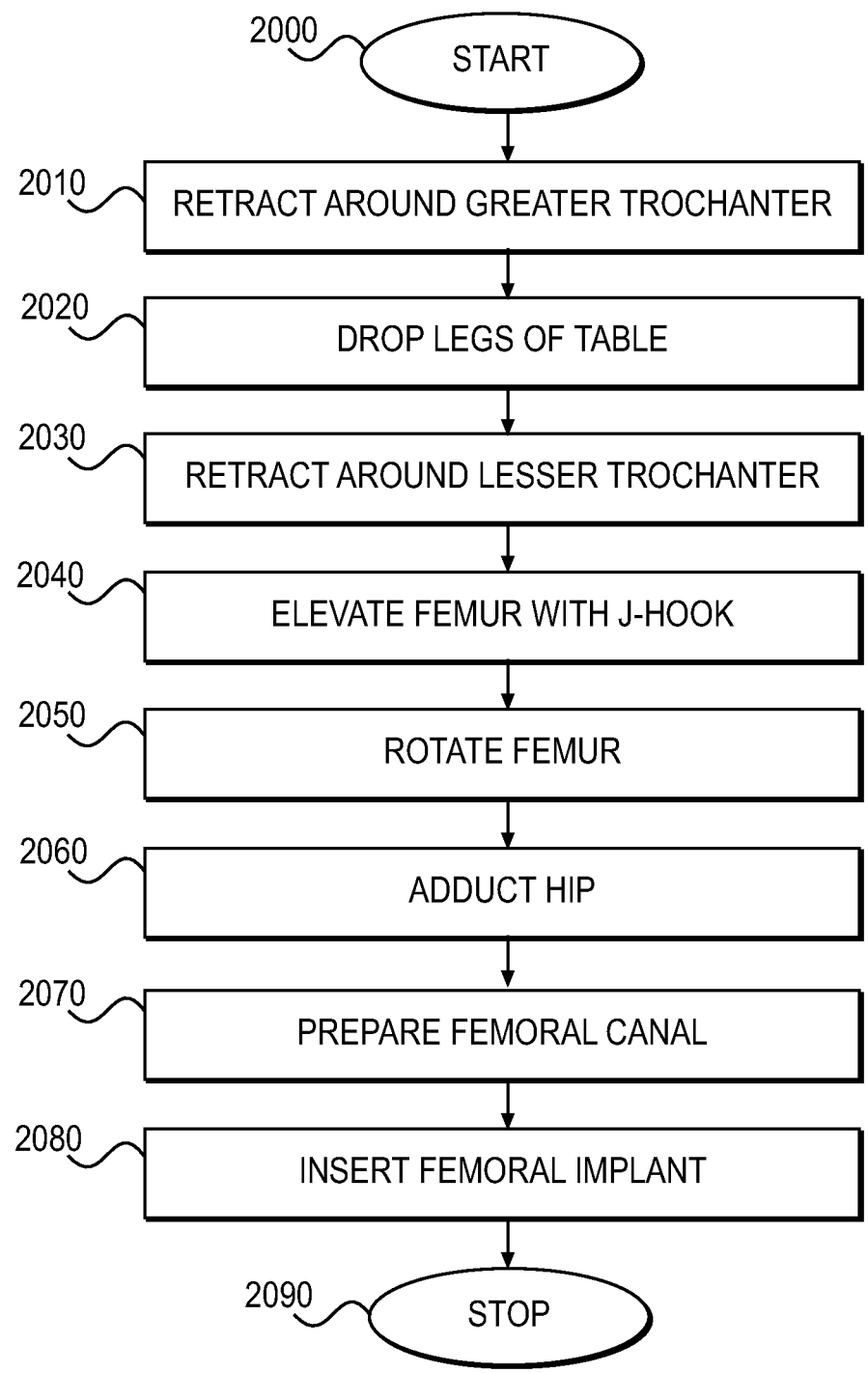
FIG. 3 illustrates a flow chart showing an exemplary method of preparing the femur for an anterior approach hip replacement.

FIG. 3 illustrates a flow chart showing a method 2000 of preparing the femur for an anterior approach hip replacement using a retractor assembly 10. The method 2000 may correspond to step 1060 of method 1000. Method 2000 may begin at step 2010 and proceed to step 2020.

In step 2020, the surgeon may retract tissue surrounding the greater trochanter using retractor 800. Retractor 800 may be a trochanteric retractor. The surgeon may use either a two-pronged trochanteric retractor or a blunt stout trochanteric retractor. The surgeon may place the trochanteric retractor 800 behind the greater trochanter. The surgeon may secure the trochanteric retractor 800 to accessory arm 110 at connector 118 and lock accessory arm 110 in place. The method may then proceed to step 2030.

In step 2030, the surgeon may drop the legs of table 12. The surgeon may lower the distal end of table 12, such that table 12 bends at the joint under the patient's hips. The non-operative leg may be supported by stand such as a well padded sterile Mayo stand when the surgeon drops the legs of table 12. Dropping the legs of table 12 may cause the patient's hip to extend approximately 30-60 degrees. The surgeon may adjust the angle of table 12 to achieve the desired angle of the hip. The method 2000 may then proceed to step 2040.

In step 2040, the surgeon may retract tissue surrounding the lesser trochanter using retractor 600. In this step, retractor 600 may be a two-pronged stout trochanteric retractor. The surgeon may place a second two-pronged stout trochanteric retractor 600 over the lesser trochanter. The second trochanteric retractor may be secured to accessory arm 60. The second trochanteric retractor 600 may retract medial soft tissues and help elevate the femur and deliver it laterally. The surgeon may lock the second trochanteric retractor 600 in place using handle 68. The method 2000 may then proceed to step 2040.

In step 2040, the surgeon may place J-hook 900 around the proximal femur at a point just distal to the lesser trochanter. The surgeon may use the pointed tip of the J-hook 900 to pierce through the gluteus maximus tendon. The surgeon may then secure J-hook 900 to ratchet femur distractor 250 at hook connection 262. The surgeon may use ratchet femur distractor 250 to slowly elevate the femur. While elevating the femur, the surgeon may carefully release the posterior hip capsule off of the posterior femoral neck. The surgeon may adjust retractors 800 and 600 to help facilitate delivery of the femur. The method 2000 may then proceed to step 2050.

In step 2050, the surgeon may place a femoral clamp directly on the proximal femoral shaft. The surgeon may then use the femoral clamp to externally rotate the femur.

The surgeon may secure the femoral clamp to a vertical side post 222 to lock the femur in the rotated orientation. The method may then proceed to step 2060.

In step 2060, the surgeon may use a loop or lasso to adduct the patient's hip. The surgeon may place the loop or lasso around the patient's thigh. The surgeon may adduct the patient's hip by pulling the thigh medially using the loop or lasso. The loop or lasso may then be attached to post 20. The femur may then be in position for preparing the femoral implant. The method 2000 may then proceed to step 2070, where the method ends.

In step 2070, the surgeon may prepare the femoral canal. The surgeon may open the canal with a box osteotome followed by a canal finder. The surgeon may use incrementally increasing sized broaches to prepare the canal. The final broaching size may match the size of the hip implant system used. The method 2000 may then proceed to step 2080.

In step 2080, the surgeon may insert the femoral implant. The femoral implant may include a femoral stem, neck piece, and head piece. The surgeon may first implant the femoral stem into the femoral canal. The surgeon may trial the implant system including both the femoral implant and the acetabular cup implant. The surgeon may trial various combinations of modular trial neck pieces and head pieces to ensure proper fit. The surgeon may also trial the acetabular cup and liner. Once the selected implants are in place, the surgeon may loosen the retractors to reduce the hip. The surgeon may test the implant by gross inspection, palpation, and range of motion for optimal stability, soft tissue tension, and limb lengths. Trial implants may be replaced until an appropriate set is found. Once an appropriate set is found, the method 2000 may proceed to step 2090, where the method ends.

Figure 4:
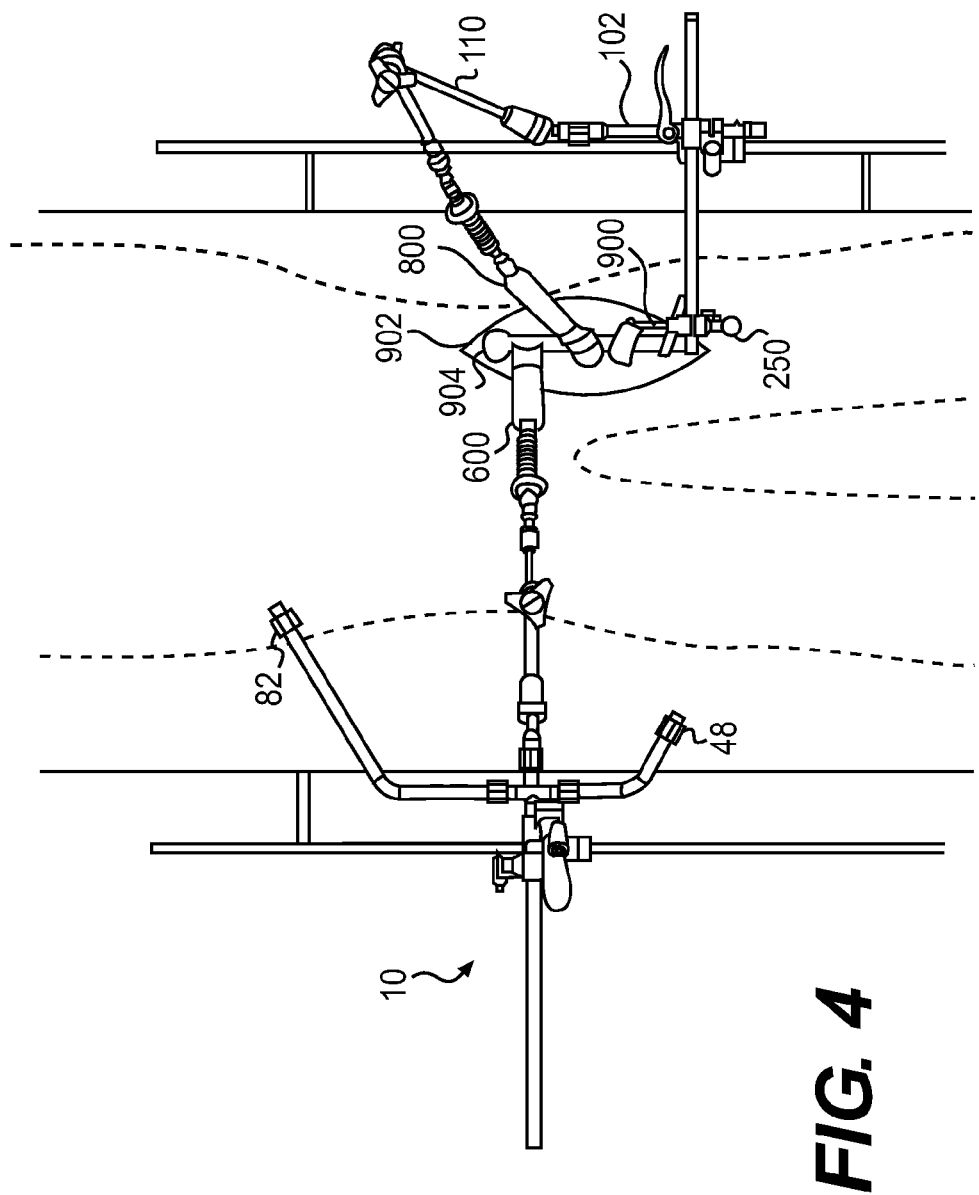
FIG. 4 illustrates an exemplary positioning of a retractor assembly during exposure of the femur.

FIG. 4 illustrates an exemplary positioning of the retractor assembly 10 during exposure of femur 904. Retractor assembly 10 may include the same components as described above regarding FIG. 1. Arm 102 may be mounted on vertical post 222 instead of post 22.

Femur 904 may be exposed through incision 902. Trochanteric retractor 800 may be inserted behind the greater trochanter. Two-pronged stout trochanteric retractor 600 may be inserted behind the lesser trochanter. Retractors 800 and 600 may retract tissue away from femur 904 while also elevating femur 904. J-hook 900 may be inserted behind femur 904 then attached to ratchet femur distractor 250. Ratchet femur distractor 250 may used to slowly elevate femur 904. Additional retractors (not shown) may be used to retract soft tissue away from the surgical site. The additional retractors may be attached to retractor assembly 10 at quick connect 48 and/or quick connect 72 via accessory arms (not shown).

Although the various exemplary embodiments have been described in detail with particular reference to certain exemplary aspects thereof, it should be understood that the invention is capable of other embodiments and its details re capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A method of anterior hip replacement, comprising:
   placing a patient in a supine position on a table;
   forming an anterior approach incision in the patient to provide access to a femoral head;
   exposing a surgical site including a femoral neck and an acetabulum;
   engaging the medial femoral neck with a first retractor;
   removing the femoral head by cutting the femoral neck;
   preparing the acetabulum for an acetabular implant;
   preparing the femur for insertion of a femoral implant including a neck piece and head piece;
   inserting the femoral implant; and
   closing the incision,
   wherein exposing the surgical site includes:
      making an incision from a spot approximately one fingerbreadth distal and lateral to the anterior superior iliac spine directed toward the lateral thigh of approximately 8-12 cm in length;
      placing the first retractor underneath the rectus femoris muscle of the femoral neck;
      retracting the sartorius and rectus femoris muscles medially;
      securing the first retractor in place by attaching the first retractor to a first accessory arm;
      placing the first retractor around the medial femoral neck;
      securing the first retractor to the first accessory arm;
      placing a second retractor laterally around the lateral femoral neck; and
      securing the second retractor to a second accessory arm; and
      cutting the femoral neck.

2. The method of anterior hip replacement of claim 1, wherein the first retractor is a hohmann retractor.

3. The method of anterior hip replacement of claim 1, wherein the step of exposing the surgical site further comprises:
   developing an interval between the tensor fascia lata and sartorius muscles;
   retracting the sartorius and rectus femoris muscles medially with the first retractor by placing the first retractor underneath the rectus femoris muscle on the medial side of the femoral neck.

4. The method of anterior hip replacement of claim 3, further comprising:
   identifying and ligating the lateral femoral circumflex artery and vein; and
   elevating the indirect head of the rectus femoris muscle, revealing an underlying hip.

5. The method of anterior hip replacement claim 1, wherein the step of preparing the femur comprises:
   positioning the femur using one or more retractors such that the femoral canal is exposed.

6. The method of anterior hip replacement of claim 5, wherein the step of preparing the femur further comprises:
   placing a J-hook around the proximal femur at a point distal to the lesser trochanter;
   securing the J-hook to a femur distractor; and
   elevating the femur using the femur distractor.

7. The method of anterior hip replacement of claim 6, wherein the step of preparing the femur further comprises:
   mounting a horizontal side bar to a vertical side post such that the horizontal side bar is directed proximally;
   mounting an accessory arm to the horizontal side bar;
   placing a trochanteric retractor behind the greater trochanter; and
   securing the trochanteric retractor to the accessory arm.

8. The method of anterior hip replacement of claim 6, wherein the step of preparing the femur further comprises:
   dropping a distal end of the table such that the hip joint is extended approximately 30-60 degrees;

placing the first retractor medially over the lesser trochanter; and securing the first retractor to a first accessory arm.

9. The method of anterior hip replacement of claim 6, wherein the step of preparing the femur further comprises:

placing a femoral clamp directly on the proximal femoral shaft;

rotating the femur using the femoral clamp; and securing the femoral clamp to the first vertical post.

10. The method of anterior hip replacement of claim 6, wherein the step of preparing the femur further comprises:

placing a loop around the thigh;

adducting the hip using the loop; and securing the loop to the first vertical post.

11. A method of anterior hip replacement, comprising:

placing a patient in a supine position on a table;

forming an anterior approach incision in the patient to provide access to a femoral head;

exposing a surgical site including a femoral neck and an acetabulum;

engaging the medial femoral neck with a first retractor;

removing the femoral head by cutting the femoral neck;

preparing the acetabulum for an acetabular implant;

preparing the femur for insertion of a femoral implant including a neck piece and head piece;

inserting the femoral implant; and closing the incision, wherein the step of preparing the acetabulum includes:

placing a second retractor at the center of the posterior wall of the acetabulum;

levering the femur posteriorly using the second retractor;

securing a second accessory arm with the second retractor;

placing the first retractor at the superior anterior wall of the acetabulum;

securing the first retractor to a first accessory arm;

placing a third retractor at the inferior anterior wall of the acetabulum;

securing the third retractor to a third accessory arm; and reaming the acetabulum.

12. The method of anterior hip replacement of claim 11, wherein the step of preparing the acetabulum further includes:

clearing the acetabulum of all pulvinar, labrum and debris; and removing the retractors.

13. The method of anterior hip replacement of claim 11, further comprising placing an acetabular cup in the reamed acetabulum.

* * * * *